United States Patent
Laufer et al.

(10) Patent No.: US 8,077,024 B2
(45) Date of Patent: Dec. 13, 2011

(54) VEHICLE COMPRISING A DISTANCE CONTROL SYSTEM

(75) Inventors: Martin Laufer, Hasloch (DE); Robert Luftner, Dorfprozelten (DE); Christian Schmidt, Erfurt (DE); Tim Weis, Mainaschaff (DE)

(73) Assignee: Magna Donnelly Engineering GmbH, Sailauf (DE)

( * ) Notice: Subject to any disclaimer, the term of this patent is extended or adjusted under 35 U.S.C. 154(b) by 468 days.

(21) Appl. No.: 11/910,586

(22) PCT Filed: Mar. 29, 2006

(86) PCT No.: PCT/DE2006/000560
§ 371 (c)(1),
(2), (4) Date: Jun. 3, 2008

(87) PCT Pub. No.: WO2006/105763
PCT Pub. Date: Oct. 12, 2006

(65) Prior Publication Data
US 2008/0266069 A1      Oct. 30, 2008

(30) Foreign Application Priority Data

Apr. 4, 2005  (DE) .......................... 10 2005 015 463

(51) Int. Cl.
*B60Q 1/00*  (2006.01)
(52) U.S. Cl. ........ 340/435; 340/436; 340/903; 340/904; 180/169; 701/301
(58) Field of Classification Search .................. 340/435, 340/436, 903, 904, 555, 438, 901, 905, 990, 340/995.1; 180/167, 169, 274; 307/10.1–10.4; 701/45, 23, 301

See application file for complete search history.

(56) References Cited

U.S. PATENT DOCUMENTS

| 4,458,446 | A | | 7/1984 | Mochida et al. | |
|---|---|---|---|---|---|
| 5,786,772 | A | * | 7/1998 | Schofield et al. | 340/903 |
| 5,793,308 | A | | 8/1998 | Rosinski | |
| 6,037,860 | A | * | 3/2000 | Zander et al. | 340/436 |
| 6,169,940 | B1 | * | 1/2001 | Jitsukata et al. | 701/23 |
| 6,693,524 | B1 | | 2/2004 | Payne | |
| 7,280,035 | B2 | * | 10/2007 | McLain et al. | 340/435 |
| 2003/0030724 | A1 | | 2/2003 | Okamoto | |
| 2005/0035879 | A1 | | 2/2005 | Gotzig et al. | |
| 2007/0165908 | A1 | | 7/2007 | Braeunl et al. | |

FOREIGN PATENT DOCUMENTS

| DE | 29806638 U1 | 7/1998 |
|---|---|---|
| DE | 10230945 | 3/2003 |
| DE | 10244148 | 4/2004 |
| DE | 10324188 | 12/2004 |
| DE | 10349755 | 1/2005 |
| FR | 2622300 | 4/1989 |
| WO | 9847022 | 10/1998 |
| WO | 9910803 | 3/1999 |
| WO | 2004/090569 A1 | 10/2004 |
| WO | 2006105763 A3 | 10/2006 |

* cited by examiner

*Primary Examiner* — Anh V La
(74) *Attorney, Agent, or Firm* — Quarles & Brady LLP

(57) ABSTRACT

The invention pertains to a vehicle (01) with a distance control system, wherein the distance control system features at least one distance sensor (08) for measuring the distance of the vehicle (01) from surrounding objects (02, 03, 05). A distance sensor (08) is arranged on at least one side of the vehicle (01) in the central region thereof, particularly in or on the exterior rearview mirror (06, 07).

17 Claims, 1 Drawing Sheet

VEHICLE COMPRISING A DISTANCE CONTROL SYSTEM

CROSS REFERENCE TO RELATED APPLICATION

This application is a U.S. national phase of PCT Application No. PCT/DE2006/000560 filed on Mar. 29, 2006, which claims priority to German Patent Application No. 10 2005 015 463.8 filed Apr. 4, 2005.

STATEMENT REGARDING FEDERALLY SPONSORED RESEARCH OR DEVELOPMENT

Not applicable.

FIELD OF THE INVENTION

The invention pertains to a vehicle with a distance control system.

BACKGROUND OF THE INVENTION

Distance control systems of this type are used in modern vehicles, for example, as a parking aid. The measured values recorded by the distance sensors are converted and can be graphically illustrated on a display arranged in the vehicle interior. In other known distance control systems, the distance of the vehicle from the leading vehicle is measured at high vehicle speeds in order to regulate the vehicle speed accordingly.

In known distance control systems, the distance sensors are typically realized in the form of ultrasonic sensors that are integrated into the bumpers. The integration into a bumper results in a relatively low installation height that, in turn, leads to ground reflections of the ultrasonic sensors. These ground reflections can falsify the measuring signal and lead to an incorrect signal evaluation. The ground reflections furthermore limit the transmission and reception range of known distance sensors such that the detection range of known distance control systems is relatively short.

SUMMARY OF THE INVENTION

Based on this state of the art, the present invention therefore aims to propose a vehicle with a novel distance control system. Another objective of the invention consists of proposing new methods for utilizing such distance control systems.

This objective is attained with a vehicle and the methods according to the independent claims.

Advantageous embodiments of the invention form the objects of the dependent claims.

The distance control system of the inventive vehicle is based on the fundamental idea of arranging the distance sensors on at least one side of the vehicle in the central region thereof rather than on the front or the rear of the vehicle. The arrangement on the side of the vehicle makes it possible to realize new measuring characteristics in the distance control and opens up new fields of application. It is possible, in particular, to measure laterally positioned parking spaces with simple means.

The distance sensor may essentially be arranged at any location on the side of the vehicle. The sensor integration on the side of the vehicle can be realized in a particularly simple and cost-efficient fashion if the distance sensor is arranged in or on the exterior rearview mirror. In this case, the sensor can be protected, in particular, from external influences by the housing of the exterior rearview mirror. In addition, the visual appearance of the vehicle is not compromised by the integration of the distance sensor into the exterior rearview mirror. It is preferred to respectively arrange one distance sensor in both exterior rearview mirrors such that measurements can be carried out on both sides of the vehicle.

The distance sensor may essentially have any type of measuring characteristic. According to one preferred embodiment, the distance sensor should, however, only determine the distance from objects that are respectively situated in a predetermined measuring plane or a measuring sector that approximately forms a measuring plane relative to the distance sensor. In other words, the distance sensor has an approximately two-dimensional measuring characteristic such that the measurement is respectively carried out in quasi sectional planes through the three-dimensional surroundings. This significantly simplifies the evaluation of the measuring data because the distance of the object from the vehicle results from the distance of the object from the distance sensor in the two-dimensional measuring plane. In order to detect three-dimensional objects, the vehicle is moved relative to the object and successive measurements are carried out in measuring planes that are spaced apart from one another. The shape and the distance of the measured object relative to the vehicle can be calculated by combining the measuring data of the different measuring planes. Corresponding processing algorithms are known from medical engineering, for example, in the field of computer-assisted tomography.

With respect to the arrangement of the measuring plane or the measuring sector relative to the vehicle, it is particularly advantageous if the measuring plane or the measuring sector extends vertically upward and/or vertically downward from the distance sensor. It is furthermore preferred that the measuring plane or the measuring sector extends perpendicular to the longitudinal axis of the vehicle.

The distance sensor on the side of the vehicle may be realized, for example, in the form of an ultrasonic sensor. Alternatively, it would also be possible and particularly preferable to realize the distance sensor in the form of an image sensor such as, for example, a camera. The distances from surrounding objects can be derived by evaluating the image data in this case. This is preferably realized with electronic image processing devices, for example, with suitable image processing software installed thereon.

In order to realize a particularly high functional integration into the exterior rearview mirrors, the image processing device can be integrated into the exterior rearview mirror in addition to the distance sensor.

Particularly reliable measuring results are obtained if predetermined image patterns in the image processing system can be compared with the image data arriving from the image sensor. This makes it possible, for example, to also detect color markings for defining parking spaces or curbstones in the recorded images such that two-dimensional parking space boundaries can also be recognized as a result. Images of the vehicle surroundings can be recorded while the vehicle is in motion and the distance traveled by the vehicle is registered. The recorded images are subsequently evaluated by means of image processing algorithms and objects situated in the vehicle surroundings are tracked from image to image. The motion vector of these objects relative to the vehicle can be determined based on this object tracking, wherein the comparison of these motion vectors with those of objects in the ground plane makes it possible to determine the position and the size of these objects.

In addition to the inventive distance sensors on the side of the vehicle, the distance control system may be designed so as to additionally comprise distance sensors that are arranged on the front and/or the rear of the vehicle.

According to a first variation of a method for operating a distance control system, the measuring data of the distance sensors can be used for detecting lateral parking spaces while searching for an appropriate parking area.

In this respect, it is particularly advantageous if measuring data is acquired in measuring planes or measuring sectors that are spaced apart from one another while the vehicle travels at a slow speed. The shape and the arrangement of three-dimensional objects in the surroundings of the vehicle can be derived from this measuring data in the individual measuring planes or measuring sectors by means of corresponding image data processing. Suitable image processing algorithms are known, for example, from the field of computer-assisted tomography.

Alternatively or additionally to the first variation of the method, the measuring data of the lateral distance sensors may also be used for deriving the maximum permissible opening angle of a vehicle door, particularly while the car is at a standstill. This makes it possible to prevent damages to the door edges and painted surfaces of laterally parking vehicles when the vehicle door is opened.

In order to prevent damages to the door edges, a first variation proposes that a warning signal is generated, for example, by means of the car horn when the vehicle door is opened and the door approaches the maximum permissible opening angle. The user opening the door is thusly alerted as to the fact that a collision between the outer door edge and a surrounding object is imminent if the door is opened any further.

As an alternative to alerting the user when the door is opened, it would also be conceivable to provide the vehicle with an actuator that restricts the door movement. This actuator may consist, for example, of an electromechanical brake in the door hinge and be controlled in dependence on the measuring data of the lateral distance sensor in such a way that the door movement automatically stops when the vehicle door is opened and approaches the maximum permissible opening angle, i.e., the door movement is restricted to a permissible degree.

BRIEF DESCRIPTION OF THE DRAWINGS

One embodiment of the invention is schematically illustrated in the figures and described in an exemplary fashion below.

The figures show.

DETAILED DESCRIPTION OF THE EXAMPLE EMBODIMENTS

Figure 1:
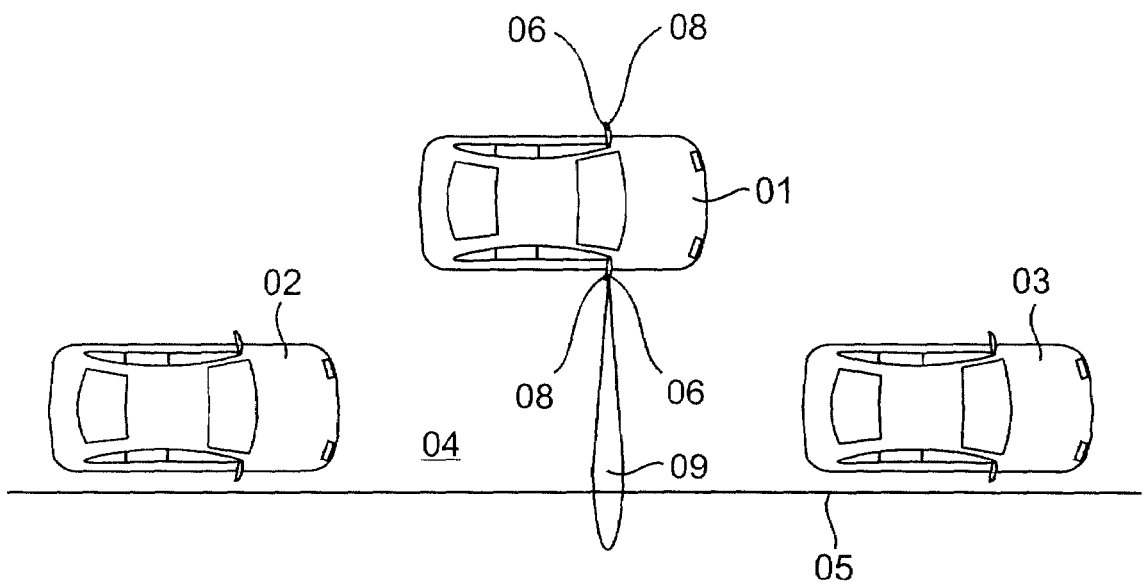
FIG. 1, a schematic top view of a driving situation while searching for a parking space, and FIG. 2, a schematic front view of the center vehicle in FIG. 1.

FIG. 1 shows a schematic top view of a vehicle 01 in a typical driving situation while searching for a parking space. A lateral parking space 04 between two vehicles 02 and 03 is bordered by a curbstone 05.

A distance control system is provided in the vehicle 01 in order to measure the dimensions of the lateral parking space 04 that is defined by the front of the vehicle 02, the rear of the vehicle 03 and the curbstone 05. Two distance sensors 08 of the distance control system of the vehicle 01 are installed in the left and the right exterior rearview mirrors 06 and 07.

The measuring range 09 of the distance sensor 08 installed in the right exterior rearview mirror 07 is illustrated in the form of a top view in FIG. 1. This figure shows that the distance sensor 08 has an approximately two-dimensional measuring characteristic. This means that the distance sensor 08 respectively measures the distance of the vehicle 01 from objects that are situated in a measuring sector with a very small aperture angle. Due to the very small aperture angle of the measuring sector, this measuring sector approximately forms a measuring plane substantially orthogonal to the side of the vehicle 01.

Figure 2:
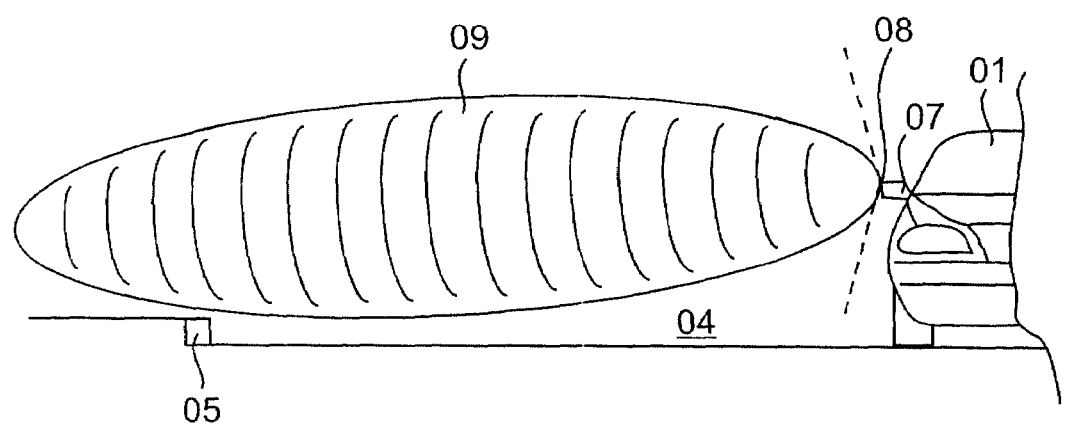

FIG. 2 shows a schematic front view of the vehicle 01, wherein the measuring range 09 is schematically indicated in this figure. Undesirable ground reflections are largely prevented due to the arrangement of the distance sensor 08 in the exterior rearview mirror 07 and the thusly realized relatively large distance from the ground.

The invention claimed is:

1. A vehicle comprising:
    a front;
    a rear spaced from said front;
    a first side joining said front and said rear, said first side having a first central region;
    a second side spaced from said first side and joining said front and said rear, said second side having a second central region; and
    a distance control system, wherein the distance control system features at least one distance sensor for measuring the distance of the vehicle from surrounding objects, wherein the at least one distance sensor is arranged on at least one side of the vehicle in the central region thereof and defines a vertical measuring plane extending substantially orthogonal relative to the at least one side of the vehicle.

2. The vehicle according to claim 1, wherein the distance sensor is arranged in or on an exterior rearview mirror mounted on the at least one side of the vehicle.

3. The vehicle according to claim 2, wherein a left exterior rearview mirror and a right exterior rearview mirror are respectively equipped with a distance sensor.

4. The vehicle according to claim 1, wherein the distance sensor has such a measuring characteristic that it only determines the distance from objects that are situated in the measuring plane or a measuring sector that approximately forms the measuring plane.

5. The vehicle according to claim 4, wherein the measuring plane or the measuring sector extends vertically upward and/or downward from the distance sensor.

6. The vehicle according to claim 1, wherein the distance sensor is realized in the form of an ultrasonic sensor.

7. The vehicle according to claim 1, wherein the distance sensor is realized in the form of an image sensor, particularly a camera, that makes it possible to record images of the lateral surroundings of the vehicle.

8. The vehicle according to claim 7, wherein the image data arriving from the image sensor is additionally processed and/or conditioned in an electronic image processing device.

9. The vehicle according to claim 8, wherein the image processing device is arranged in or on an exterior rearview mirror mounted on the at least one side of the vehicle.

10. The vehicle according to claim 7, wherein predetermined image patterns in the image processing system can be compared with image data arriving from the image sensor.

11. The vehicle according to claim 1, wherein at least one distance sensor is provided on the rear and/or on the front of the vehicle in addition to the at least one distance sensor arranged on the at least one side of the vehicle.

12. A method for operating a distance control system, particularly in a vehicle according to claim 1, wherein the size and/or the arrangement of a lateral parking space is derived from the measuring data of the distance sensor.

13. The method according to claim 12, wherein the distance sensor records measuring data in measuring planes or measuring sectors that are spaced apart from one another while the vehicle travels at a slow speed, wherein the shape and the arrangement of objects in the surroundings of the vehicle are derived from the measuring data.

14. A method for operating a distance control system, particularly in a vehicle according to claim 1, wherein the maximum permissible opening angle of a vehicle door is derived from the measuring data of the distance sensor, particularly while the car is at a standstill.

15. The method according to claim 14, wherein a warning signal is generated when the vehicle door is opened and approaches the maximum permissible opening angle.

16. The method according to claim 14, wherein the door movement is restricted by an actuator when the vehicle door is opened and approaches the maximum permissible opening angle.

17. The vehicle as in claim 1, in which an exterior rearview mirror is mounted on the at least one side of the vehicle.

* * * * *